United States Patent
Cazaux et al.

(10) Patent No.: US 9,575,039 B2
(45) Date of Patent: Feb. 21, 2017

(54) CURVED GASEOUS PARTICLE DETECTOR

(71) Applicant: Commissariat a l'energie atomique et aux energies alternatives, Paris (FR)

(72) Inventors: Sandrine Cazaux, Montlhery (FR); Thierry Lerch, Alfortville (FR); Stephan Aune, Palaiseau (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 305 days.

(21) Appl. No.: 14/054,150

(22) Filed: Oct. 15, 2013

(65) Prior Publication Data

US 2014/0102173 A1    Apr. 17, 2014

(30) Foreign Application Priority Data

Oct. 15, 2012    (FR) .................................... 12 59799

(51) Int. Cl.
    *G01N 33/00*    (2006.01)
    *G01T 1/185*    (2006.01)
    *H01J 47/02*    (2006.01)

(52) U.S. Cl.
    CPC ........... *G01N 33/0009* (2013.01); *G01T 1/185* (2013.01); *H01J 47/02* (2013.01); *Y10T 428/24025* (2015.01)

(58) Field of Classification Search
    CPC .......... G01T 5/12; G01T 1/185; G01T 1/2935; Y10T 428/24025; H01J 47/02
    See application file for complete search history.

(56) References Cited

U.S. PATENT DOCUMENTS

| 3,703,638 A | | 11/1972 | Allemand et al. | |
| 4,031,396 A | * | 6/1977 | Whetten ................. | H01J 47/02 250/374 |
| 4,553,062 A | * | 11/1985 | Ballon .................... | H01J 47/02 250/385.1 |
| 4,583,331 A | * | 4/1986 | Hunt ....................... | E04H 15/18 135/132 |
| 4,625,117 A | * | 11/1986 | Hayakawa .............. | H01J 47/02 250/374 |
| 5,027,564 A | * | 7/1991 | Lechner ................ | E04B 1/3211 52/2.23 |
| 6,011,265 A | | 1/2000 | Sauli | |

(Continued)

FOREIGN PATENT DOCUMENTS

FR    2 786 024    5/2000

OTHER PUBLICATIONS

Search Report and Written Opinion as issued for French Patent Application No. 1259799, dated Sep. 5, 2013.

(Continued)

*Primary Examiner* — Lisa Caputo
*Assistant Examiner* — Punam Roy
(74) *Attorney, Agent, or Firm* — Pillsbury Winthrop Shaw Pittman LLP

(57) ABSTRACT

A curved gaseous particle detector includes a stack of two layers that are curved and maintained together by a frame formed of two spars defining a plane. The two spars are connected together by at least two curved bars outside of the plane and the frame being placed between the two layers of the stack.

13 Claims, 3 Drawing Sheets

(56) References Cited

U.S. PATENT DOCUMENTS

| | | | |
|---|---|---|---|
| 7,078,704 B2* | 7/2006 | Lacy | G01T 1/2935 250/375 |
| 8,745,928 B2* | 6/2014 | Greiner | B64C 1/066 52/3 |
| 2003/0002626 A1* | 1/2003 | Hoheisel | A61B 6/032 378/98.8 |
| 2010/0193691 A1* | 8/2010 | Ishii | H01L 27/14663 250/366 |
| 2012/0049054 A1* | 3/2012 | Zhou | B82Y 15/00 250/265 |

OTHER PUBLICATIONS

Fenker, H., et al., "BoNus: Development and use of a radial TPC using cylindrical GEMs," Nuclear Instruments and Methods in Physics Research, Section A: Accelerators, Spectrometers, Detectors, and Associated Equipment, vol. 592, No. 3, Jul. 21, 2008, pp. 273-286.

Balla, A., et al., "Status of the cylindrical-GEM project for the KLOE-2 inner tracker," Nuclear Instruments and Methods in Physics Research, Section A: Accelerators, Spectrometers, Detectors, and Associated Equipment, vol. 628, No. 1, 2011, pp. 194-198.

Bencivenni, G., et al., "The Full Scale Prototype of the Cylindrical-GEM Detector as Inner Tracker in KLOE2," IEEE Nuclear Science Symposium Conference Record, 2007, pp. 4666-4670.

* cited by examiner

CURVED GASEOUS PARTICLE DETECTOR

CROSS REFERENCE TO RELATED APPLICATIONS

This application claims the benefit of priority from French Patent Application No. 1259799 filed on Oct. 15, 2012, the entire content of which is incorporated herein by reference.

FIELD

An aspect of the invention relates to a gaseous particle detector, particularly detectors referred to as "micro-megas detectors" (for "MICRO MEsh GAseous Structure") or detectors known as GEM (for "Gas Electron Multiplier").

BACKGROUND

Detectors D for locating particles are known, such as that illustrated in FIG. 1 comprising a gas enclosure 1 that is filled with an appropriate gaseous mixture, such a detector D enabling the amplification of electrons by an avalanche process. Such a detector is particularly disclosed by the document FR2786024. In this particular case, the particles are photons.

The gaseous mixture contained in the enclosure 1 may remain confined in the enclosure 1 or circulate through a purifier (not illustrated) through pipes 2.

This enclosure 1 is closed in a sealed manner by a window 3 transparent to the photons 4 to be detected. The detector D also comprises an electrically insulating plate 5 of very good flatness, on which is formed the active part of the detector D, in particular elementary anodes 6 which may be parallel metal tracks or metal elements that may be referred to as "pixels" and which form a two-dimensional network on the electrically insulating plate 5. The set of tracks constitutes the anode 7 of the detector D. The tracks are earthed and are connected to suitable electronic means 8 provided for amplifying then processing the electrical signals coming from these tracks.

Moreover, this active part comprises, facing the window 3, a cathode 9 constituted of a metal sheet pierced with holes 10, said sheet thereby forming a grid. The anode 7 and the grid 9 are maintained parallel to each other by means of electrically insulating spacers 11 that rest on the anode 7.

Polarisation means 12 are moreover provided to take the grid 9 (in other words the cathode) to a highly negative voltage compared to the anode 7 (this voltage depending on the gaseous mixture used). The anode 7, which is thus taken to a high potential compared to the cathode 9, constitutes with the latter a detector with parallel electrodes capable of amplifying electrons by an avalanche process that develops between these electrodes. In the example represented, the high voltage is chosen to create in the space A comprised between the anode 7 and the cathode 9, or amplification space, an electric field EA of which the intensity is greater than or equal to 50 kV/cm.

In the case of the detection of non-ionising particles such as photons, it is necessary to add a conversion layer 13 to convert the non-ionising particles into ionising particles.

This type of particle detector nevertheless has drawbacks. In fact, when it is desirable to obtain a curved structure, it is necessary to join up end to end a plurality of flat structures so as to obtain a curved surface. This particularity does not make it possible in any case to obtain a compact or even light detector.

SUMMARY

In this context, an aspect of the present invention is to provide a gaseous particle detector that is both compact and light.

To this end, an embodiment of the invention relates to a curved gaseous particle detector comprising a stack of two layers. These layers are curved and maintained together by a frame formed of two spars defining a plane, the two spars being connected together by at least two curved bars outside of the plane, the frame being placed between the two layers of the stack.

Such a curved detector has a self-supporting structure that forms an integral part of the detector, the elements forming the frame make it possible at one and the same time to form a detection space, to maintain the two layers joined together and to stiffen the detector. These particularities make it possible not only to reduce the weight of the detector but also to increase its compactness.

The detector according to an embodiment of the invention may also have one or more of the following characteristics, considered individually or according to any technically possible combination thereof.

In a non-limiting embodiment of the detector, the two layers are transparent to more than 99% of the particles to be detected.

In a non-limiting embodiment of the detector, the two layers are formed of:
  a first support layer, and
  a second layer, referred to as drift layer, the first layer comprising an outer face facing the second layer, the outer face supporting an active detection part.

In a non-limiting embodiment of the detector, the active detection part comprises an amplification device.

In a non-limiting embodiment of the detector, the frame is made of a material of which the Young's modulus is greater than 30 GPa.

In a non-limiting embodiment of the detector, the frame is made of carbon.

In a non-limiting embodiment of the detector, at least one of the spars is hollow so that gas can pass through it, the at least one hollow spar further comprising at least one orifice emerging into the detection zone of the detector comprised between the two layers. In this embodiment, the at least one hollow spar may have at each of its ends a gas connection.

In a non-limiting embodiment of the detector, the two curved bars are parallel to each other and have a continuous curve.

In a non-limiting embodiment of the detector, a joint is arranged on the circumference of the detector so as to ensure the sealing of said detector. The joint may for example have a thickness of at least 1 mm.

In a non-limiting embodiment of the detector, each spar and each curved bar have a same constant thickness such that the two layers are equidistant.

In a non-limiting embodiment of the detector, the outer face of the second layer forms an outer detection face of another detector arranged above the second layer.

In a non-limiting embodiment of the detector, the first layer and the second layer are positioned with respect to each other by means of at least two pins, each of the two pins passing through the first and second layers and the curved bars.

In a non-limiting embodiment of the detector, electronic connection plugs are fixed on the first layer, each of the plugs comprising an elastic mechanism so as to improve the electrical contact between the plugs and the detector.

The subject matter of another aspect of the invention is also a structure for maintaining a plurality of detectors. The structure comprises:
 a first plate,
 a second plate transparent to the particles to be detected, the first plate and the second plate being connected together by a slide system transparent to the particles to be detected that it is desirable to detect, the slide system being adapted to receive a plurality of detectors according to an embodiment the invention.

BRIEF DESCRIPTION OF THE DRAWINGS

Other characteristics and benefits of the invention will become clearer from the description that is given thereof below, by way of indication and in no way limiting, and by referring to the appended figures, among which.

In all of the figures, common elements bear the same reference numbers.

DETAILED DESCRIPTION

Figure 1:
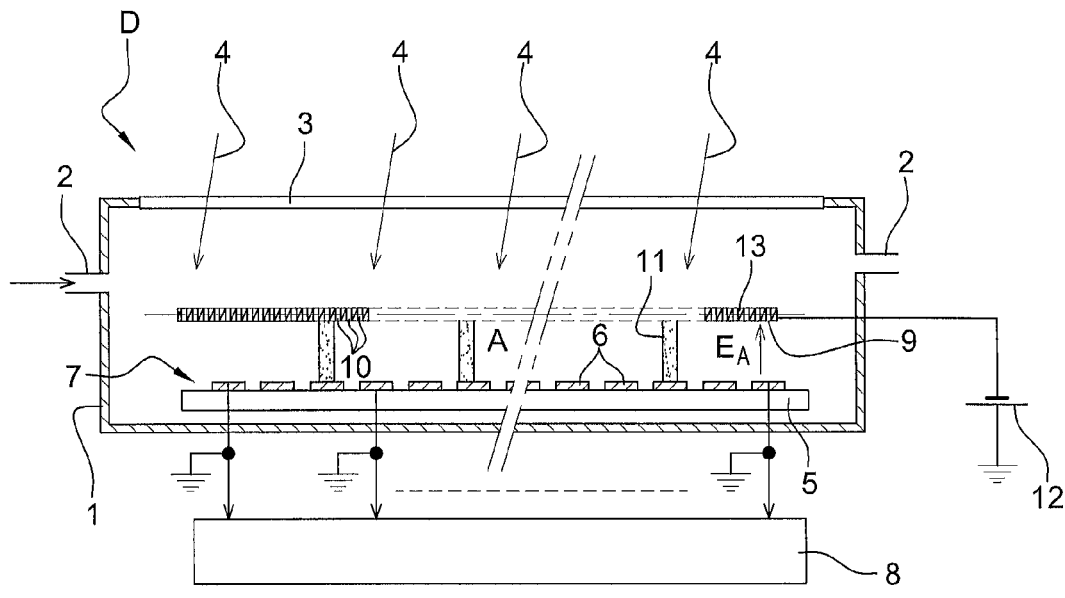
FIG. 1 schematically illustrates a detector for locating particles with gaseous filling according to the prior art.

FIG. 1 has already been detailed to illustrate a detector for locating particles with gaseous filling according to the prior art.

Figure 2:
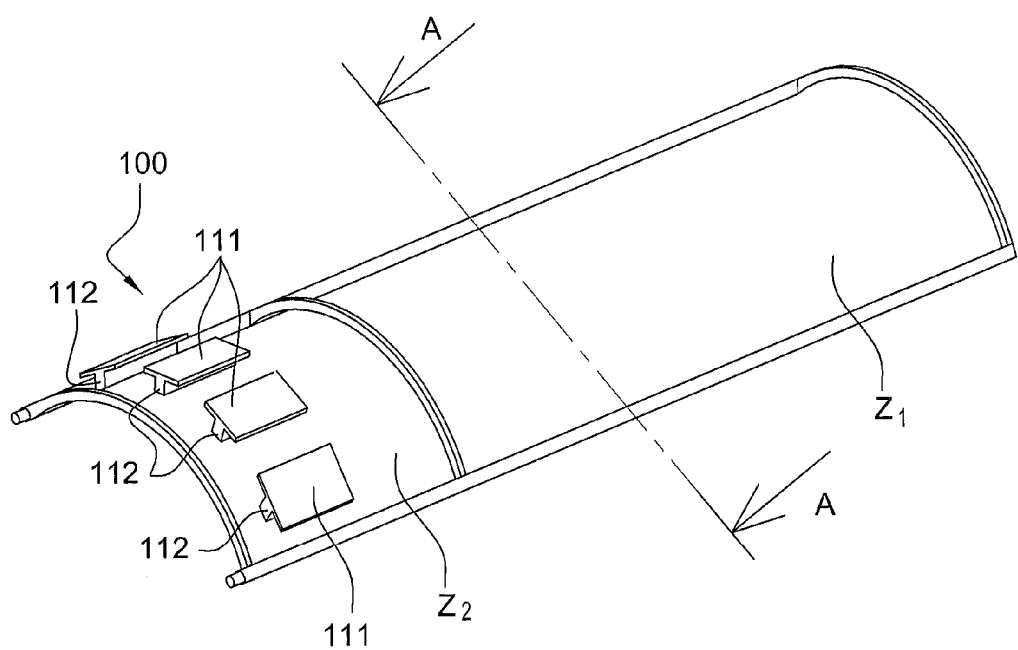
FIG. 2 illustrates a non-limiting embodiment of a curved gaseous particle detector according to an embodiment of the invention.
Figure 3:
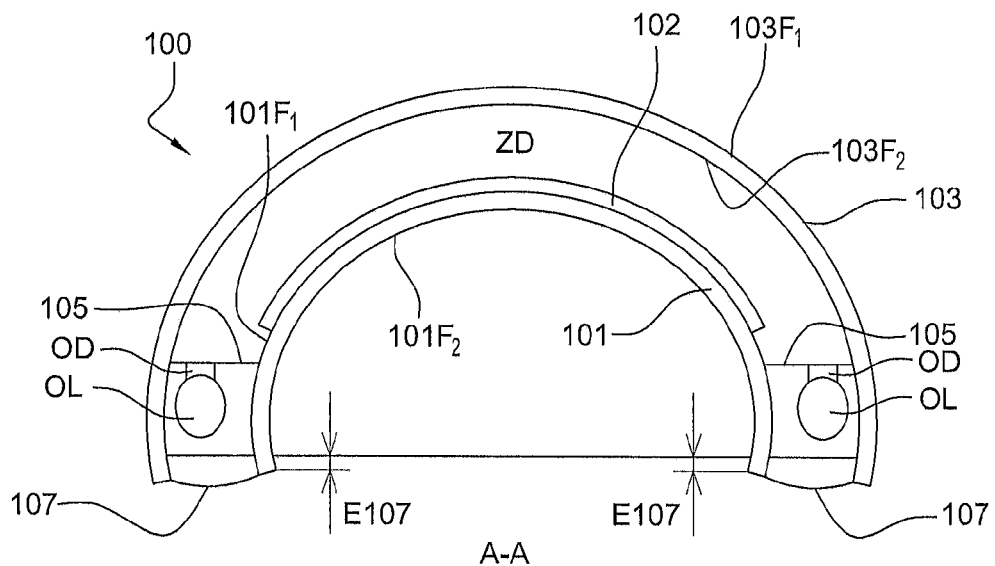
FIG. 3 illustrates a sectional view of a curved gaseous particle detector according to that which is represented in FIG. 2.

FIG. 2 illustrates a first non-limiting embodiment of a curved gaseous particle detector 100 also known as micromegas detector for "MICRO MEsh GAseous Structure" according to an aspect of the invention. FIG. 3 is a sectional view along A-A of the curved gaseous particle detector 100 illustrated in FIG. 2.

The gaseous particle detector 100 comprises a stack of two layers 101 and 103. These layers 101 and 103 are curved and are maintained together by a frame 104 according to that illustrated in FIG. 4. It will be noted that the frame 104 is positioned between the two layers 101 and 103 of the stack.

Figure 4:
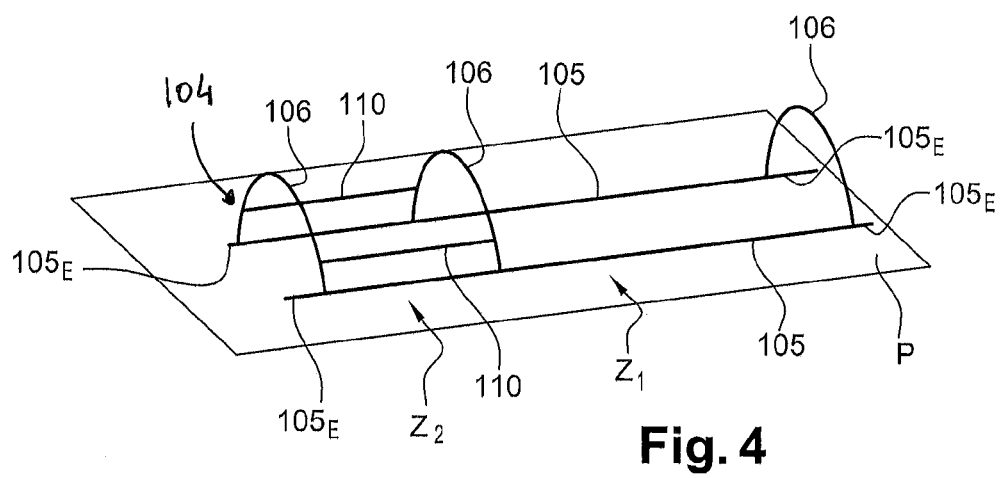
FIG. 4 illustrates a non-limiting embodiment of a frame of a curved gaseous particle detector according to that illustrated in FIG. 2.

In the example of embodiment of the frame 104 illustrated in FIG. 4, the frame 104 comprises two spars 105 (or straight bars) and three curved bars 106 (or arches). The two spars 105 define a plane P, and are connected together by means of three curved bars 106. It will be noted that the three curved bars 106 are outside of this plane P. The radius of curvature of the curved bars 106 depends on the desired curve.

The material of the frame 104 may be in a non-limiting manner carbon. Other materials may be envisaged, it is desirable that these materials have a Young's modulus greater than 30 GPa in order to have a sufficient rigidity to be self-supporting. Kevlar, aluminium or stainless steel are materials having such characteristics.

Carbon is desired for its qualities as much in terms of mechanical and physical performances. In fact, this material has a low density (around 1900 kg/m3), a high Young's modulus (around 110 GPa), a high tensile strength (around 1000 MPa) and a high radiation length (around 302 mm). Carbon thus makes it possible to form a frame 104 that is at one and the same time rigid, light and transparent to the particles.

In this embodiment, the spars 105 are hollow so that gas can pass through them. As illustrated in the sectional view A-A, the spars 105 are traversed in their length by a longitudinal orifice OL. Each spar 105 also has emerging orifices OD (only two are represented) both in the longitudinal orifice OL and in the detection zone ZD of the detector 100. This detection zone ZD is comprised between the two layers 101 and 103. The longitudinal OL and emerging OD orifices make to possible to convey gas, via the spars 105, into the detector 100. Each hollow spar 105 comprises at each of its ends 105E a gas connection (not illustrated). These gas connections may for example be inserted and bonded in the spars 105, more particularly inserted and bonded in the longitudinal orifices OL.

In a non-limiting example, the two spars 105 have a square section of dimension 3×3 mm and a length L of 658 mm.

It will be noted that the three curved bars 106 are substantially parallel to each other and have a continuous curve. These three curved bars 106 have for example a thickness of 3 mm, i.e. a thickness identical to that of the spars 105. In other words, the two layers 101 and 103 are equidistant.

These three curved bars 106 moreover have a determined radius of curvature.

The two layers 101 and 103 that the gaseous particle detector 100 comprises are formed by:
 a first support layer 101, and
 a second layer 103, referred to as drift later.

The first support layer 101' is formed for example of a sheet of Kapton™, PCB, multilayer PCB type or other having a thickness for example of 200 µm. The first layer 101 comprises an outer face 101F1 facing the second layer 103. This outer face 101F1 supports an active detection part 102. This active detection part 102 may comprise an amplification device. The amplification device is for example:
 a grid for Micromegas detectors,
 a stack of amplification sheets for GEM detectors.

The inner face 101F2 of the first layer 101 may support connection tracks or be metallised to serve as electromagnetic shielding.

The second layer 103 is, for example, formed of a Kapton™, PCB, Mylar™ type sheet. This second layer 103 has for example a thickness of the order of 200 µm. It is desirable that this second layer 103 have conduction properties for establishing the drift potential. It may be made of any material of which:
 the outer face 103F1 may be covered with a conductive material serving as electromagnetic shielding, and
 the inner face 103F2 is covered with a conductive material to constitute the drift layer.

Generally speaking, the thickness of the layers will be determined as a function of the Young's modulus of the material used. It will have to be thin enough so that the material can be curved and thick enough so that the structure does not collapse on itself. For example, for a structure of dimensions of the order of 50 cm (length of the spars), layers made of PCB will be comprised between 60 and 100 μm and layers made of Kapton will be comprised between 100 and 150 μm.

It may be noted that the frame 104, which is arranged between the two layers 101 and 103, forms a spacer drift. The frame 104 made of carbon is positioned and bonded on the first layer 101, and the second layer 103 is positioned and bonded on the frame 104 made of carbon.

In the example described, each curved bar 106 and each spar 105 has a thickness of the order of 3 mm so as to space the first layer 101 and the second layer 103 apart by a distance of 3 mm, this distance being desirable to carry out a detection of particles.

It will be appreciated that such a distance is not limiting and that the frame 104 may have a thickness greater than or less than 3 mm.

In a non-limiting embodiment, a joint 107 is arranged on the circumference of the detector 100 so as to assure the sealing of the detector 100. The joint 107 may for example be formed by a strip of adhesive arranged on the circumference of the detector 100 between the first layer 101 and the second layer 103. This strip of adhesive forming the joint 107 may have a thickness E107 of at least 1 mm. This adhesive is insulating, resistant and transparent to the particles to be detected.

Figure 5:
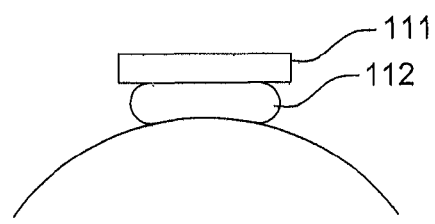
FIG. 5 illustrates an embodiment of a connection plug that comprises a curved gaseous particle detector according to that illustrated in FIG. 2.

Moreover, the detector 100 comprises an active zone Z1 and a connection zone Z2. The connection zone Z2 is stiffened for example by other spars 110 bonded on the first layer 101 and connecting the curved bars 106 (see FIG. 4) so as to be able to assemble and dismantle the connectors without weakening the detector 100. This connection zone Z2 comprises electronic connection plugs 111, each of the plugs 111 comprises elastic mechanism 112 so as to improve the contacts between the detector 100 and the plug 111 without forcing the layer 101 to compensate the radius of curvature (see FIG. 5). The elastic mechanism 112 may include an elastic element that is adapted to elastically deform.

Figure 6:
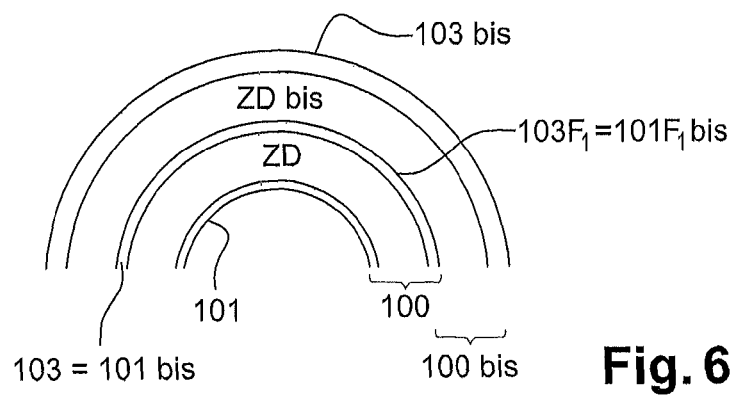
FIG. 6 illustrates an embodiment of two curved gaseous particle detectors arranged one on top of the other, each curved particle detector being according to that illustrated in FIG. 2.

In an embodiment of the invention illustrated in FIG. 6, the outer face 103F1 of the second layer 103 forms a detection face 101F1 bis of another detector 100 bis arranged above the second layer 103 of the detector 100. In other words, according to this embodiment, the second layer 103 of a detector 100 also acts as first layer 101 bis of another detector 100 bis.

Figure 7:
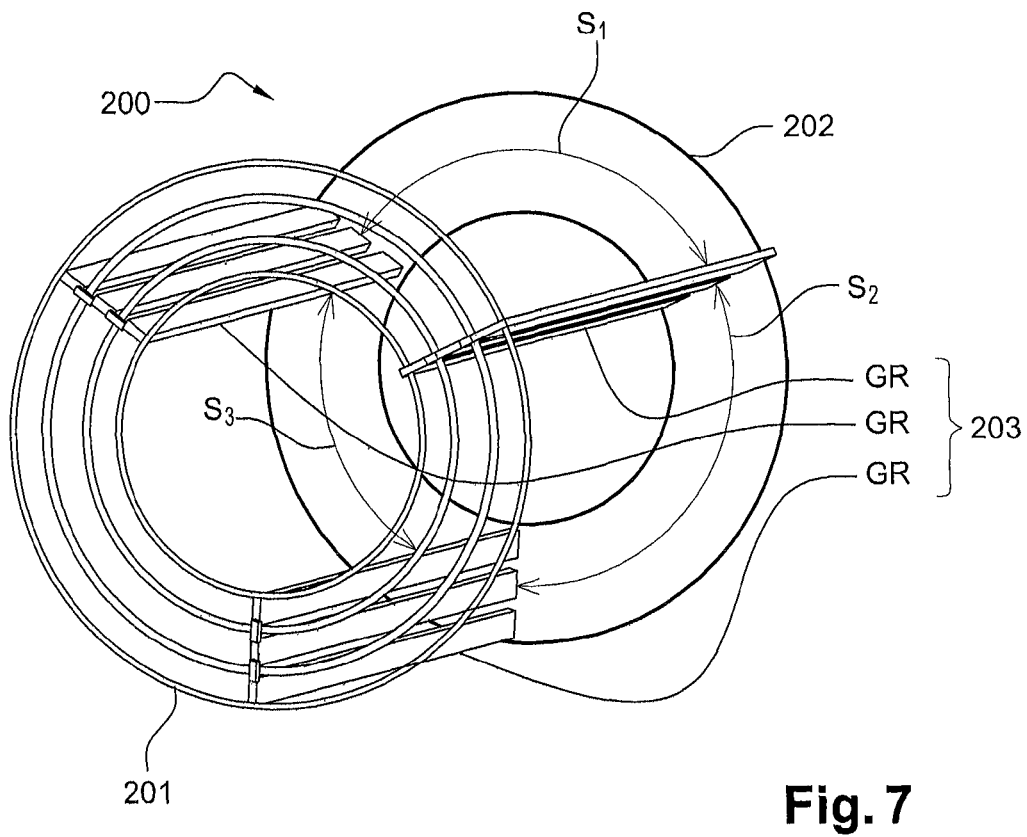
FIG. 7 illustrates a non-limiting embodiment of a structure for maintaining a plurality of curved detectors according to that illustrated in FIG. 2.

The subject matter of another aspect of the invention is also a structure 200 for maintaining a plurality of detectors 100 according to the invention, such a maintaining structure 200 being represented in a schematic manner in FIG. 7.

In fact, if the detector has a very high radius of curvature and/or a very large surface, it will probably not be possible to form a cylindrical detector: it will then be constituted of an assembly of several sectors of detectors, for example here 3 (each sector of detectors being formed of a detector 100 according to the invention).

The maintaining structure 200 comprises a first plate 201 and a second plate 202, this second plate 202 being transparent to the particles that it is wished to detect.

The first plate 201 and the second plate 202 are connected together by a slide system 203 also transparent to the particles that it is wished to detect, the slide system 203 being adapted to receive a plurality of detectors 100 according to the invention. The material of the slide system 203 may be carbon. Since the slide system 203 is situated in the detection zone, this system 203 is transparent to the particles to be detected.

In this non-limiting example, the slide system 203 is formed of three groups of rails GR. These groups of rails GR divide the cylinder of the maintaining structure 200 into three sectors S1, S2, S3, each of the sectors S1, S2 and S3 being able to receive six detectors 100 according to an embodiment of the invention. To do this, the six detectors 100 are slid between two groups of rails. These six detectors 100 thereby positioned are superimposed one on the other in a same sector. In other words, such a maintaining structure 200 is adapted to maintain eighteen detectors 100 according to the invention.

The first plate 201 situated at one end of the structure 200 is for example made of aluminium and has an openwork design so as to allow the assembly and the dismantling of the detectors 100. Moreover, this first plate 201 has an openwork design so as to reduce the weight of the structure 200.

Conversely, the second plate 202 is, in a non-limiting manner, solid and is for example made of carbon transparent to the particles that it is desirable to detect (this transparency is desirable since it is situated at the level of the detection zone of the structure 200). This second plate 202 obstructs one of the ends of the structure 200 while assuring the sealing thereof.

Moreover, the first plate 201 and the second plate 202 stiffen the maintaining structure 200.

It will be noted that the maintaining structure 200 makes it possible to insert, position and support for example six layers of detectors per sector S1, S2, S3.

Moreover, the maintaining structure 200 may also support a plurality of flat gaseous particle detectors. In this case, the flat detectors are positioned in the detection zone and at the level of the second plate 202.

In other words, this maintaining structure 200 enables the precise positioning of all types of detector (curved and flat detectors) to constitute cylinders constituting the maintaining structure 200 and to stiffen the assembly to obtain little deformation of the assembly and detectors so as to be able to position precisely and always in the same position the detectors (in the case of a change of defective detectors 100 for example).

Moreover, due to the use of carbon, a minimum of material and dead zones are present. Carbon combines lightness, transparency, good mechanical properties and thermal insulation.

Moreover, it will be noted that the use of curved detectors makes it possible to increase the detection zone.

It will moreover be noted that each curved detector 100 has a self-supporting structure. In fact, the elements composing it are bonded together (space gain), the gas passes through the mechanics (weight, volume of material gain). The detector 100 is compact and the dead zones are limited.

While specific embodiments of the invention have been described above, it will be appreciated that the invention may be practiced otherwise than as described. The descriptions above are intended to be illustrative, not limiting. Thus, it will be appreciated by one skilled in the art that modifications may be made to the invention as described without departing from the scope of the claims set out below.

The invention claimed is:

1. A curved gaseous particle detector comprising a stack of two layers, wherein said two layers are curved and maintained together by a frame formed of two spars defining a plane, said two spars being connected together by at least two curved bars outside of said plane, the frame being placed between said two layers of the stack in order to form a detection zone between said two layers for receiving a gas, and an active detection part to detect particles, wherein the two layers are transparent to more than 99% of the particles to be detected.

2. The curved gaseous particle detector according to claim 1, wherein the two layers are formed of:
   a first support layer, and
   a second layer,
   said first layer comprising an outer face facing said second layer, said outer face supporting the active detection part.

3. The curved gaseous particle detector according to claim 2, wherein the active detection part comprises an amplification device.

4. The curved gaseous particle detector according to claim 2, wherein an outer face of the second layer forms an outer detection face of another detector arranged above said second layer.

5. The curved gaseous particle detector according to claim 2, wherein the first layer and the second layer are positioned with respect to each other by means of at least two pins, each of said two pins passing through said first and second layers and the curved bars.

6. The curved gaseous particle detector according to claim 2, wherein electronic connection plugs are fixed on the first layer, each of the plugs comprising an elastic mechanism so as to improve the electrical contact between the plugs and the detector.

7. The curved gaseous particle detector according to claim 1, wherein the frame is made of a material of which the Young's modulus is greater than 30 GPa.

8. The curved gaseous particle detector according to claim 1, wherein the at least two curved bars are substantially parallel to each other and have a continuous curve.

9. The curved gaseous particle detector according to claim 1, wherein a joint is arranged on the perimeter of said detector so as to assure the sealing of said detector.

10. A curved gaseous particle detector comprising a stack of two layers, wherein said two layers are curved and maintained together by a frame formed of two spars defining a plane, said two spars being connected together by at least two curved bars outside of said plane, the frame being placed between said two layers of the stack in order to form a detection zone between said two layers for receiving a gas, and an active detection part to detect particles, wherein the frame is made of carbon.

11. A curved gaseous particle detector comprising a stack of two layers, wherein said two layers are curved and maintained together by a frame formed of two spars defining a plane, said two spars being connected together by at least two curved bars outside of said plane, the frame being placed between said two layers of the stack in order to form a detection zone between said two layers for receiving a gas, and an active detection part to detect particles, wherein at least one of the spars is hollow so that gas can pass through it, said at least one hollow spar further comprising at least one orifice emerging into the detection zone of the detector comprised between the two layers.

12. A curved gaseous particle detector comprising a stack of two layers, wherein said two layers are curved and maintained together by a frame formed of two spars defining a plane, said two spars being connected together by at least two curved bars outside of said plane, the frame being placed between said two layers of the stack in order to form a detection zone between said two layers for receiving a gas, and an active detection part to detect particles, wherein a joint is arranged on the perimeter of said detector so as to assure the sealing of said detector, wherein each spar and each curved bar have a same constant thickness such that the two layers are equidistant.

13. A structure for maintaining a plurality of detectors, said structure comprising:
   a first plate,
   a second plate transparent to the particles to be detected, said first plate and said second plate being connected together by a slide system transparent to the particles to be detected, said slide system being adapted to receive a plurality of curved gaseous particle detectors that each comprise a stack of two layers, wherein said two layers are curved and maintained together by a frame formed of two spars defining a plane, said two spars being connected together by at least two curved bars outside of said plane, the frame being placed between said two layers of the stack in order to form a detection zone between said two layers for receiving a gas, and an active detection part to detect particles.

* * * * *